United States Patent [19]

Natarajan et al.

[11] Patent Number: 4,623,729

[45] Date of Patent: Nov. 18, 1986

[54] ACYLALKYLAMINOCARBONYL SUBSTITUTED AMINO AND IMINO ACID COMPOUNDS

[75] Inventors: Sesha I. Natarajan, Neshanic Station; Eric M. Gordon, Pennington, both of N.J.

[73] Assignee: E. R. Squibb & Sons, Inc., Princeton, N.J.

[21] Appl. No.: 400,798

[22] Filed: Jul. 22, 1982

[51] Int. Cl.$^4$ ........................................ C07D 213/60
[52] U.S. Cl. .................... 546/256; 562/439; 564/153; 546/147; 564/154; 564/155; 546/262; 564/157; 564/162; 546/265; 564/170; 564/176; 546/273; 564/177; 564/179; 546/276; 564/183; 564/184; 546/281; 564/185; 564/186; 548/336; 548/342; 548/356; 548/454; 548/455; 548/456; 548/463; 548/467; 548/468; 548/517; 548/525; 548/527; 548/533; 548/409; 549/59; 549/60; 549/72; 549/76; 549/77; 549/473; 549/487; 549/496; 560/16; 560/34; 560/159; 562/426

[58] Field of Search .............. 564/185, 153, 154, 155, 564/157, 162, 170, 176, 177, 179, 183, 184, 186; 546/256, 262, 265; 548/336, 342, 467; 549/59-60, 72, 76, 77, 473, 487, 496

[56] References Cited

U.S. PATENT DOCUMENTS

| | | | |
|---|---|---|---|
| 4,053,651 | 10/1977 | Ondetti et al. | 548/342 |
| 4,105,776 | 8/1978 | Ondetti et al. | 548/342 |
| 4,129,566 | 12/1978 | Ondetti et al. | 546/326 |
| 4,154,935 | 5/1979 | Ondetti et al. | 546/189 |
| 4,192,878 | 3/1980 | Ondetti | 548/215 |
| 4,199,512 | 4/1980 | Ondetti et al. | 546/223 |
| 4,217,359 | 8/1980 | Krapcho | 546/187 |
| 4,234,489 | 11/1980 | Ondetti et al. | 548/342 |
| 4,256,751 | 3/1981 | Hayashi et al. | 546/147 |
| 4,296,033 | 10/1981 | Petrillo et al. | 546/223 |
| 4,296,113 | 10/1981 | Ondetti | 546/188 |
| 4,311,697 | 1/1982 | Krapcho | 546/188 |
| 4,316,905 | 2/1982 | Krapcho | 546/256 |
| 4,316,906 | 2/1982 | Ondetti et al. | 548/342 |
| 4,329,473 | 5/1982 | Almquist et al. | 546/281 |
| 4,470,973 | 9/1984 | Natarajan et al. | 424/177 |

FOREIGN PATENT DOCUMENTS

| | | |
|---|---|---|
| 868532 | 7/1978 | Belgium . |
| 12401 | 6/1980 | European Pat. Off. . |
| 18549 | 11/1980 | European Pat. Off. . |
| 45161 | 2/1982 | European Pat. Off. . |
| 5151555 | 11/1980 | Japan . |
| 2027025 | 2/1980 | United Kingdom . |
| 2048863 | 12/1980 | United Kingdom . |

OTHER PUBLICATIONS

Meyer, et al., "Chemical Abstracts", vol. 97, 1982 col. 97:56247f.
Sen, et al., "Chemical Abstracts", vol. 61, 1964, col. 1791h–1792e.
Almquist et al., "Synthesis and Biological Activity ... Angiotensin Converting Enzyme", J. Med. Chem., 1980, 23, pp. 1392–1398.
Meyer et al., "Novel Synthesis of (S)-1-[5-(Benzoylamino)-1,4-Dioxo-6-Phenylhexyl]-L-Proline", J. Med. Chem. 1981, 24 pp. 964–969.
Sen et al., "Studies of Amino Acyl Insertion", Jour. Indian Soc., vol. 41, pp. 137–141 (1964).

*Primary Examiner*—Richard L. Raymond
*Assistant Examiner*—James H. Turnipseed
*Attorney, Agent, or Firm*—Lawrence S. Levinson; Stephen B. Davis

[57] ABSTRACT

Compounds of the formula

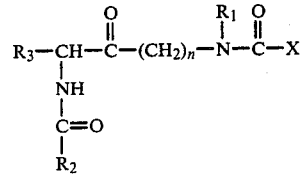

are disclosed. These compounds are useful as hypotensive agents due to their angiotensin converting enzyme inhibition activity and depending upon the definition of X may also be useful as analgesics due to their enkephalinase inhibition activity.

3 Claims, No Drawings

ACYLALKYLAMINOCARBONYL SUBSTITUTED AMINO AND IMINO ACID COMPOUNDS

BACKGROUND OF THE INVENTION

Almquist et al., "Synthesis and Biological Activity of a Ketomethylene Analogue of a Tripeptide Inhibitor of Angiotensin Converting Enzyme", J. Med. Chem., 1980, 23 1392-1398, disclose the ketomethylene compound of the formula

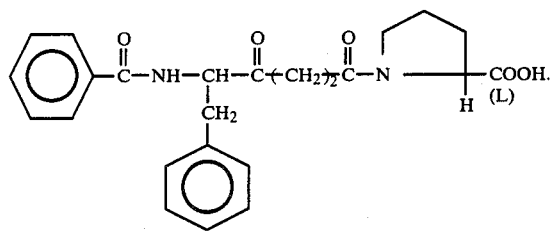

This and related compounds are also disclosed by Almquist et al. in U.S. Pat. No. 4,329,473.

Meyer et al., "Novel Synthesis of (S)-1-[5-(Benzoylamino)-1,4-dioxo-6-phenylhexyl]-L-proline and Analogues: Potent Angiotensin Converting Enzyme Inhibitors", J. Med. Chem., 1981, 24, 964–969, disclosed the synthesis and activity of compounds of the formula

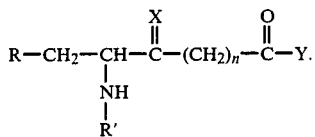

Gravestock et al. in European Patent Application 45161 disclose hypotensive compounds of the formula

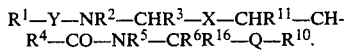

Mercaptoacyl derivatives of proline and substituted prolines are known to be useful hypotensive agents due to their angiotensin converting enzyme inhibition activity. Ondetti, et al. in U.S. Pat. No. 4,105,776 disclose such compounds wherein the proline ring is unsubstituted or substituted by an alkyl or hydroxy group. Ondetti, et al. in U.S. Pat. No. 4,154,935 disclose such compounds wherein the proline ring is substituted with one or more halogens. Ondetti, et al. in U.S. Pat. No. 4,316,906 disclose such compounds wherein the proline ring is substituted by various ethers and thioethers. Krapcho in U.S. Pat. No. 4,217,359 disclose such compounds wherein the proline ring has a carbamoyloxy substituent. Krapcho in U.S. Pat. No. 4,311,697 discloses compounds wherein the proline ring has a diether, dithioether, ketal or thioketal substituent in the 4-position. Krapcho in U.S. Pat. No. 4,316,905 discloses such compounds wherein the proline ring has a cycloalkyl, phenyl, or phenyl-lower alkylene substituent. Ondetti, et al. in U.S. Pat. No. 4,234,489 disclose such compounds wherein the proline has a keto substituent in the 5-position. Krapcho, et al. in U.S. Ser. No. 162,341 filed June 23, 1980, now U.S. Pat. No. 4,310,461, disclose such compounds wherein the proline has an imido, amido, or amino substituent in the 4-position. Iwao, et al. in U.K. Patent Application 2,027,025 disclosed such compounds wherein the propline has an aromatic substituent in the 5-position.

Mercaptoacyl derivatives of 3,4-dehydroproline are disclosed as angiotensin converting enzyme inhibitors by Ondetti in U.S. Pat. No. 4,129,566. Mercaptoacyl derivatives of thiazolidinecarboxylic acid and substituted thiazolidinecarboxylic acid are disclosed as angiotensin converting enzyme inhibitors by Ondetti in U.S. Pat. No. 4,192,878 and by Yoshitomo Pharmaceutical Ind. in Belgium Pat. No. 868,532.

Mercaptoacyl derivatives of dihydroisoindole carboxylic acids and tetrahydroisoquinoline carboxylic acids are disclosed as being useful hypotensive agents by Ondetti et al., in U.S. Ser. No. 69,031, filed Aug. 23, 1979. These mercaptoacyl tetrahydroisoquinoline compounds are also disclosed by Portlock in U.K. Application No. 2,048,863 and by Hayashi et al. in U.S. Pat. No. 4,256,751.

Mercaptoacyl derivatives of various amino acids are disclosed by Ondetti et al. as being useful hypotensive agents due to their angiotensin converting enzyme inhibition activity in U.S. Pat. No. 4,053,651.

Carboxyalkylaminocarbonyl substituted tetrahydroisoquinolines and prolines are disclosed as possessing angiotensin converting enzyme inhibition activity by Tanabe in European Patent application No. 18,549 and Japanese Patent Application No. 5151-555.

SUMMARY OF THE INVENTION

The novel acylalkylaminocarbonyl substituted amino and imino acids, esters, and salts of this invention are of the formula

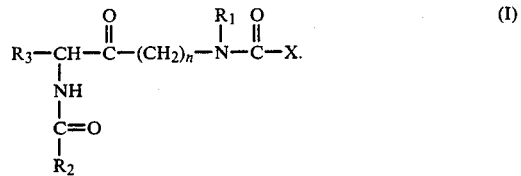

X is an amino or imino acid or ester of the formula

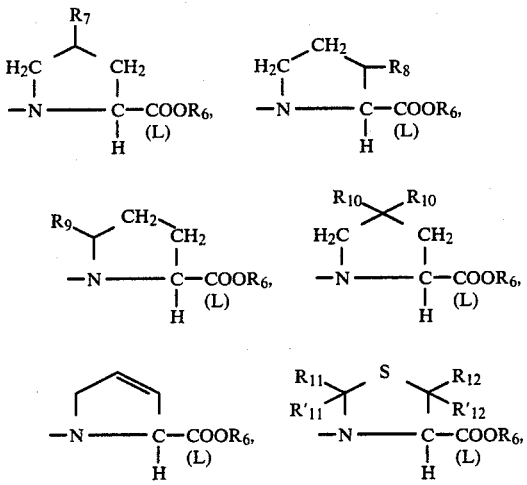

-continued

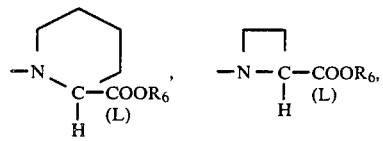

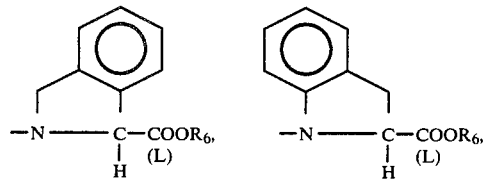

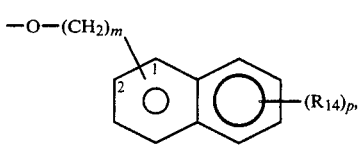

—O—lower alkyl, a 1- or 2-naphthyloxy of the formula

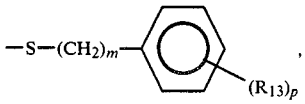

a 1- or 2-naphthyloxy of the formula

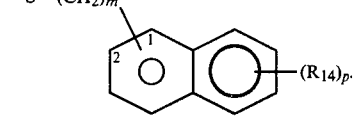

—S—lower alkyl,

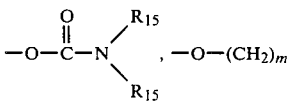

or a 1- or 2-naphthylthio of the formula

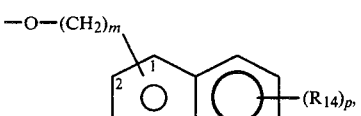

$R_7$ is hydrogen, lower alkyl, halogen, keto, hydroxy,

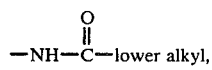

azido, amino,

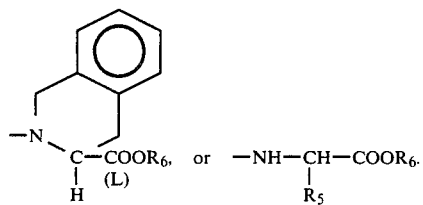

$R_8$ is keto, halogen,

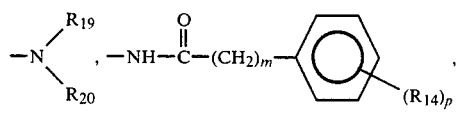

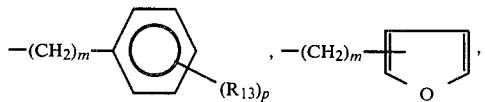

a 1- or 2-naphthyl of the formula

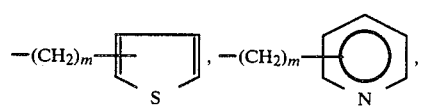

—(CH$_2$)$_m$—cycloalkyl,

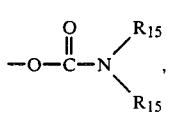

—O—lower alkyl,

—O—lower alkyl, a 1- or 2-naphthyloxy of the formula

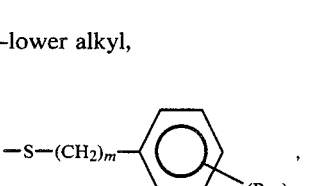

—S—lower alkyl,

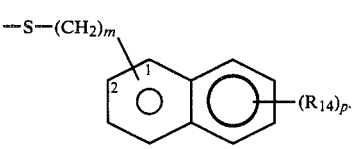

or a 1- or 2-naphthylthio of the formula $R_9$ is keto or

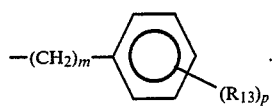

R$_{10}$ is halogen or —Y—R$_{16}$.

R$_{11}$, R$_{11}'$, R$_{12}$ and R$'_{12}$ are independently selected from hydrogen and lower alkyl or R$'_{11}$, R$_{12}$ and R$'_{12}$ are hydrogen and R$_{11}$ is

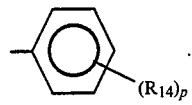

R$_{13}$ is hydrogen, lower alkyl of 1 to 4 carbons, lower alkoxy of 1 to 4 carbons, lower alkylthio of 1 to 4 carbons, chloro, bromo, fluoro, trifluoromethyl, hydroxy, phenyl, phenoxy, phenylthio, or phenylmethyl.

R$_{14}$ is hydrogen, lower alkyl of 1 to 4 carbons, lower alkoxy of 1 to 4 carbons, lower alkylthio of 1 to 4 carbons, chloro, bromo, fluoro, trifluoromethyl, or hydroxy.

m is zero, one, two, three, or four.

p is one, two or three provided that p is more than one only if R$_{13}$ or R$_{14}$ is hydrogen, methyl, methoxy, chloro, or fluoro.

R$_{15}$ is hydrogen or lower alkyl of 1 to 4 carbons.

Y is oxygen or sulfur.

R$_{16}$ is lower alkyl of 1 to 4 carbons,

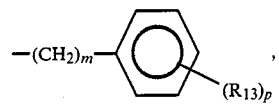

or the R$_{16}$ groups join to complete an unsubstituted 5- or 6-membered ring or said ring in which one or more of the carbons has a lower alkyl of 1 to 4 carbons or a di(lower alkyl of 1 to 4 carbons) substituent.

R$_5$ is hydrogen, lower alkyl,

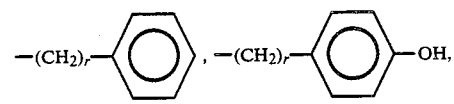

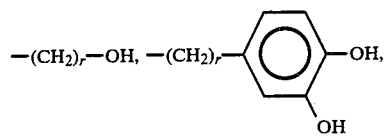

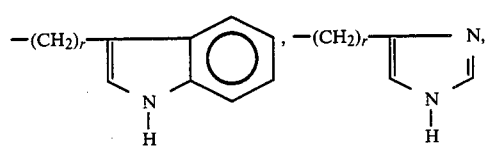

—(CH$_2$)$_r$—NH$_2$, —(CH$_2$)$_r$—SH, —(CH$_2$)$_r$—S—lower alkyl,

-continued

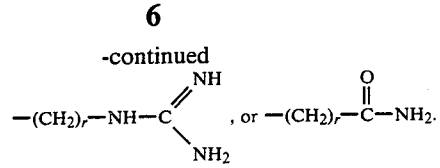

r is an integer from 1 to 4.

R$_{19}$ is lower alkyl, benzyl, or phenethyl.

R$_{20}$ is hydrogen, lower alkyl, benzyl or phenethyl.

n is one or two.

R$_1$ is hydrogen, lower alkyl, halo substituted lower alkyl,

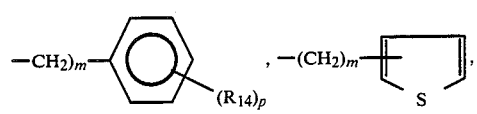

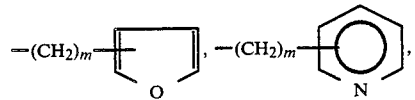

—(CH$_2$)$_m$—cycloalkyl, —(CH$_2$)$_2$—NH$_2$, —(CH$_2$)$_3$—NH$_2$,

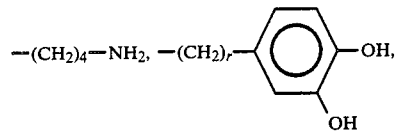

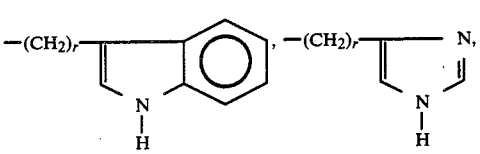

—(CH$_2$)$_r$—SH, —(CH$_2$)$_r$—OH, —(CH$_2$)$_r$—S—lower alkyl,

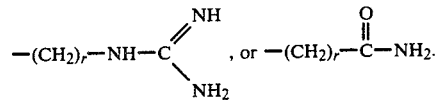

R$_2$ is 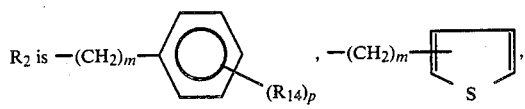

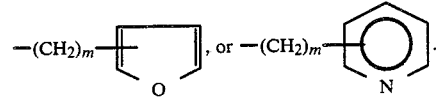

R$_3$ is hydrogen, lower alkyl, 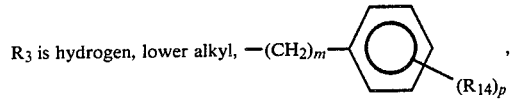

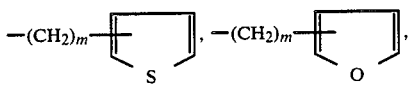

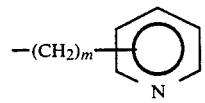

halo substituted lower alkyl, —(CH$_2$)$_m$—cycloalkyl,

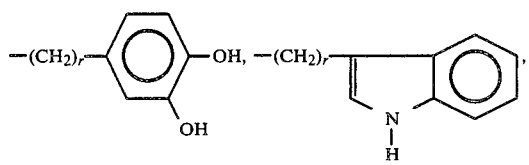

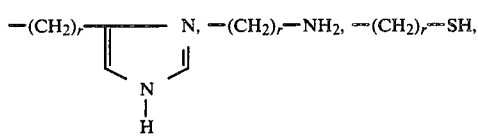

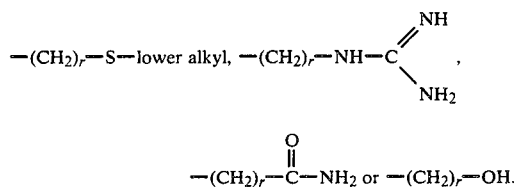

R$_6$ is hydrogen, lower alkyl, benzyl, benzhydryl, or

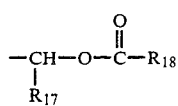

wherein R$_{17}$ is hydrogen, lower alkyl, cycloalkyl or phenyl, and R$_{18}$ is hydrogen, lower alkyl, lower alkoxy, phenyl, or R$_{17}$ and R$_{18}$ taken together are —(CH$_2$)$_2$—, —(CH$_2$)$_3$—, —CH=CH, or

DETAILED DESCRIPTION OF THE INVENTION

This invention is directed to the various novel acylalkylaminocarbonyl substituted amino and imino acid compounds of formula I above, intermediates for preparing such compounds, and compositions and methods of using compositions containing these novel compounds.

The term lower alkyl used in defining various symbols refers to straight or branched chain radicals having up to seven carbons. The preferred lower alkyl groups are up to four carbons with methyl and ethyl most preferred. Similarly the terms lower alkoxy and lower alkylthio refer to such lower alkyl groups attached to an oxygen or sulfur.

The term cycloalkyl refers to saturated rings of 3 to 7 carbon atoms with cyclopentyl and cyclohexyl being most preferred.

The term halogen refers to chloro, bromo and fluoro.

The term halo substituted lower alkyl refers to such lower alkyl groups described above in which one or more hydrogens have been replaced by chloro, bromo, or fluoro groups such as trifluoromethyl, which is preferred, pentafluoroethyl, 2,2,2-trichloroethyl, chloromethyl, bromomethyl, etc.

The symbols

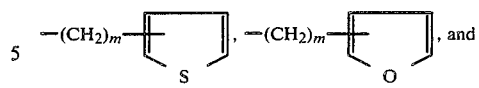

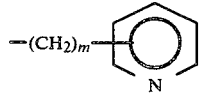

represent that the alkylene bridge is attached to an available carbon atom.

The compounds of formula I can be prepared by coupling an acylated alkylamine of the formula

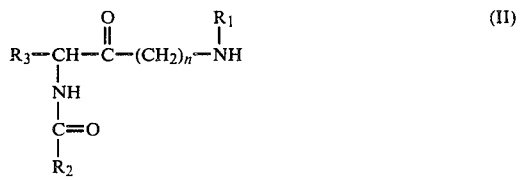

particularly the hydrochloride salt with the acid chloride of the formula

in the presence of N-methyl morpholine wherein R$_6$ in the definition of X is an easily removable ester protecting group such as benzyl or t-butyl. Removal of the R$_6$ protecting group such as by hydrogenation when R$_6$ is benzyl or treatment with trifluoroacetic acid when R$_6$ is t-butyl yields the products of formula I wherein R$_6$ is hydrogen.

The reactant of formula II can be prepared by converting the carboxyalkylamine of the formula

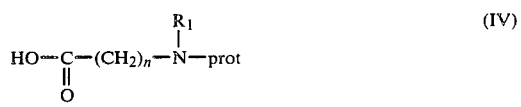

wherein prot is a protecting group such as benzyloxycarbonyl, to its acid chloride and then reacting with an oxazolone of the formula

to yield

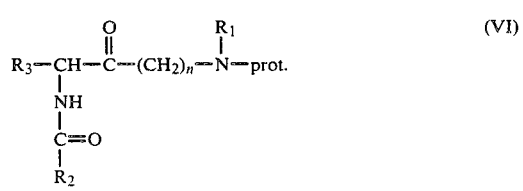

Removal of the protecting group such as by hydrogenation yields the reactant of formula II.

The reactant of formula II wherein $R_1$ is other than hydrogen can also be prepared by reacting a ketone of the formula

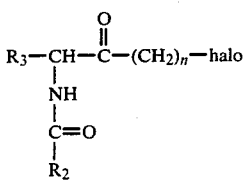 (VII)

wherein halo is Cl or Br with a substituted amine of the formula $R_1\text{—}NH_2.$ (VIII)

The ketone intermediate of formula VII can be prepared by treating a ketone of the formula

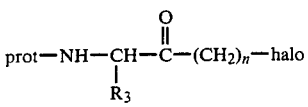 (IX)

wherein prot is a protecting group such as benzyloxycarbonyl with hydrogen bromide and acetic acid followed by reaction with the acid halide of the formula

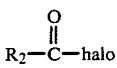 (X)

in the presence of base such as sodium bicarbonate.

The compounds of formula I can also be obtained by reacting a carboxyalkylaminocarbonyl substituted amino or imino acid chloride of the formula

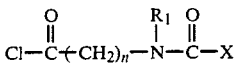 (XI)

wherein $R_6$ in the definition of X is an easily removable ester protecting group such as benzyl or t-butyl with the oxazolone of formula V. Removal of the $R_6$ ester group yields the compounds of formula I wherein $R_6$ is hydrogen.

The reactants of formula XI can be obtained by treating a substituted amine of the formula

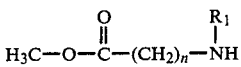 (XII)

with the acid chloride of formula III to yield

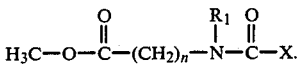 (XIII)

Treatment with methanol and sodium hydroxide, followed by oxalyl chloride yields the reactant of formula XI.

The acid chloride amino or imino acid ester of formula III is prepared by treating the corresponding amino or imino acid ester hydrochloride with phosgene in the presence of N-methyl morpholine.

In the above reactions if any or all of $R_1$, $R_3$ and $R_5$ are

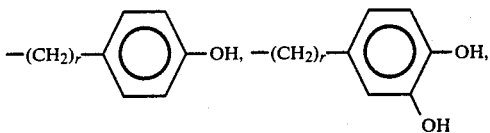

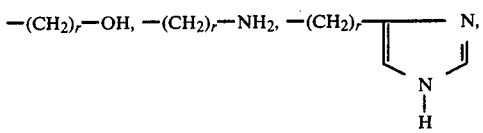

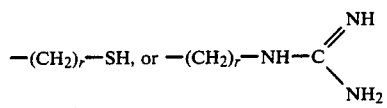

then the hydroxyl, amino, imidazolyl, mercaptan or guanidinyl function should be protected during the reaction. Suitable protecting groups include benzyloxycarbonyl, t-butoxycarbonyl, benzyl, benzhydryl, trityl, etc., and nitro in the case of guanidinyl. The protecting group is removed by hydrogenation, treatment with acid, or other known methods following completion of the reaction.

The ester products of formula I wherein $R_6$ is lower alkyl, benzyl or benzhydryl can be chemically treated such as with sodium hydroxide in aqueous dioxane or with trimethylsilylbromide to yield the products of formula I wherein $R_6$ is hydrogen. The benzyl and benzhydryl esters can also be hydrogenated, for example by treating with hydrogen in the presence of a palladium on carbon catalyst.

The ester products of formula I wherein $R_6$ is

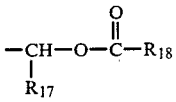

may be obtained by employing the acid chloride of formula III in the above reactions with such ester group already in place. Such ester reactants can be prepared by treating the corresponding amino or imino acid of the formula

HX (XIV)

wherein $R_6$ is hydrogen with an acid chloride such as

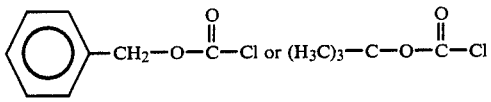

so as to protect the N-atom. The protected amino or imino acid is then reacted in the presence of a base with a compound of the formula

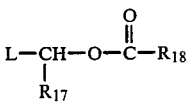 (XV)

wherein L is a leaving group such as chlorine, bromine, tolylsulfonyl, etc., followed by removal of the N- protecting group such as by treatment with acid or hydrogenation.

The ester products of formula I wherein $R_6$ is

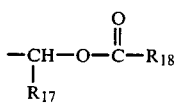

can also be obtained by treating the product of formula I wherein $R_6$ is hydrogen with a molar excess of the compound of formula XV.

The products of formula I wherein $R_7$ is amino may be obtained by reducing the corresponding products of formula I wherein $R_7$ is azido.

Preferred compounds of this invention with respect to the amino or imino acid or ester part of the structure of formula I are those wherein:

$R_5$ is hydrogen, straight or branched chain lower alkyl of 1 to 4 carbons, —$CH_2$—OH,

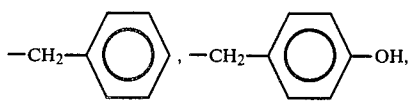

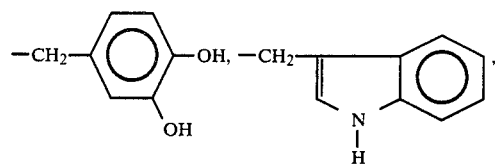

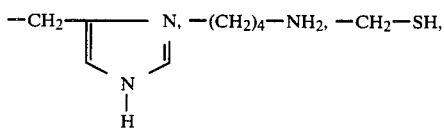

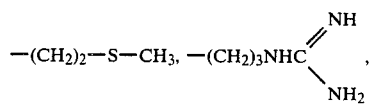

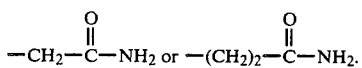

$R_6$ is hydrogen, an alkali metal salt, straight or branched chain lower akyl of 1 to 4 carbons, or

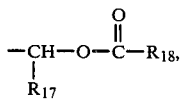

$R_{17}$ is hydrogen, straight or branched chain lower alkyl of 1 to 4 carbons, or cyclohexyl and $R_{18}$ is straight or branched chain lower alkyl of 1 to 4 carbons or phenyl.

$R_7$ is hydrogen.
$R_7$ is hydroxy.
$R_7$ is straight or branched chain lower alkyl of 1 to 4 carbons or cyclohexyl.
$R_7$ is amino.
$R_7$ is —O—lower alkyl wherein lower alkyl is straight or branched chain of 1 to 4 carbons.
$R_7$ is

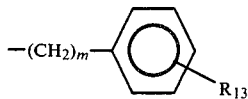

wherein m is zero, one or two and $R_{13}$ is hydrogen, methyl, methoxy, methylthio, chloro, bromo, fluoro, or hydroxy.

$R_7$ is

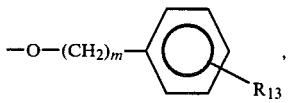

1-naphthyloxy or 2-naphthyloxy wherein m is zero, one, or two and $R_{13}$ is hydrogen, methyl, methoxy, methylthio, chloro, bromo, fluoro, or hydroxy.

$R_7$ is —S—lower alkyl wherein lower alkyl is straight or branched chain of 1 to 4 carbons.

$R_7$ is

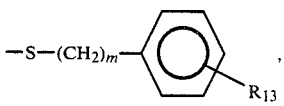

1-naphthylthio, or 2-naphthylthio wherein m is zero, one, or two and $R_{13}$ is hydrogen, methyl, methoxy, methylthio, chloro, bromo, fluoro, or hydroxy.

$R_8$ is —O—lower alkyl wherein lower alkyl is straight or branched chain of 1 to 4 carbons.

$R_8$ is

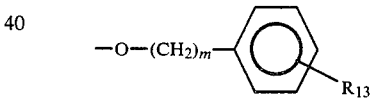

wherein m is zero, one, or two and $R_{13}$ is hydrogen, methyl, methoxy, methylthio, chloro, bromo, fluoro, or hydroxy.

$R_8$ is —S—lower alkyl wherein lower alkyl is straight or branched chain of 1 to 4 carbons.

$R_8$ is

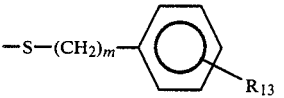

wherein m is zero, one or two and $R_{13}$ is hydrogen, methyl, methoxy, methylthio, chloro, bromo, fluoro or hydroxy.

$R_9$ is phenyl, 2-hydroxyphenyl, or 4-hydroxyphenyl.
$R_{10}$ are both fluoro or chloro.
$R_{10}$ is both —Y—$R_{16}$ wherein Y is O or S, $R_{16}$ is straight or branched chain lower alkyl of 1 to 4 carbons or the $R_{16}$ groups join to complete an unsubstituted 5- or 6-membered ring or said ring in which one or more of the available carbons has a methyl or dimethyl substituent.

$R_{11}$, $R_{11}'$, $R_{12}$ and $R_{12}'$ are all hydrogen, or $R_{11}$ is phenyl, 2-hydroxyphenyl, or 4-hydroxyphenyl and $R_{11}'$, $R_{12}$ and $R_{12}'$ are hydrogen.

Most preferred compounds of this invention with respect to the amino or imino acid or ester part of the structure of formula I are those wherein:

X is

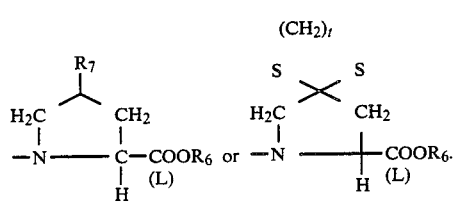

$R_6$ is hydrogen,

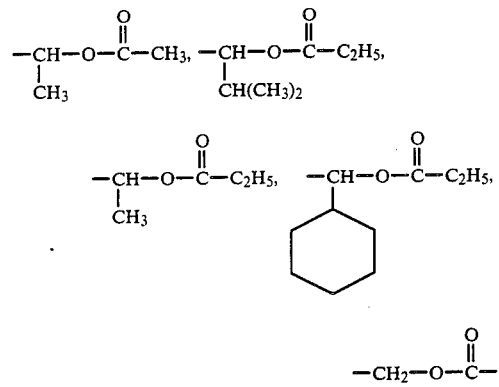

an alkali metal salt, or $-C_2H_5$.

$R_7$ is hydrogen, cyclohexyl, lower alkoxy of 1 to 4 carbons,

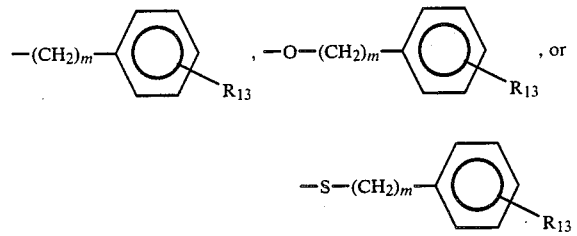

wherein m is zero, one, or two and $R_{13}$ is hydrogen, methyl, methoxy, methylthio, Cl, Br, F, or hydroxy, especially preferred wherein $R_7$ is hydrogen.

t is two or three, especially where t is two.

Preferred compounds of this invention with respect to the acylalkylaminocarbonyl portion of the structure of formula I are those wherein:

$R_1$ is straight or branched chain lower alkyl of 1 to 4 carbons, $-CF_3$, $-(CH_2)_2-NH_2$, $-(CH_2)_3-NH_2$, $-(CH_2)_4-NH_2$, $-CH_2-OH$,

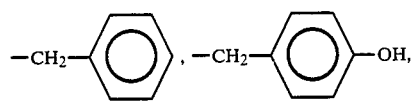

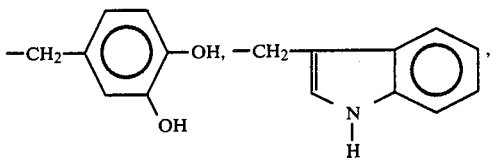

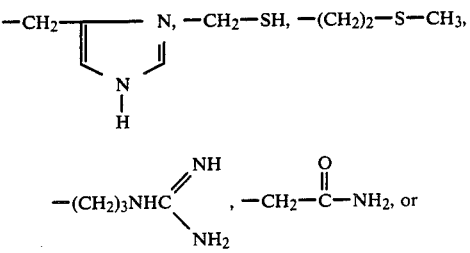

$R_2$ is

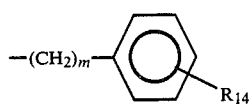

wherein m is zero, one, or two and $R_{14}$ is hydrogen, methyl, methoxy, methylthio, Cl, Br, F, or hydroxy, especially phenyl.

$R_3$ is

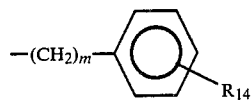

wherein m is zero, one, or two and $R_{14}$ is hydrogen, methyl, methoxy, methylthio, Cl, Br, F, or hydroxy, especially benzyl.

The compounds of formula I wherein $R_6$ is hydrogen form salts with a variety of inorganic or organic bases. The nontoxic, pharmaceutically acceptable salts are preferred, although other salts are also useful in isolating or purifying the product. Such pharmaceutically acceptable salts include alkali metal salts such as sodium, potassium or lithium, alkaline earth metal salts such as calcium or magnesium, and salts derived from amino acids such as arginine, lysine, etc. The salts are obtained by reacting the acid form of the compound with an equivalent of the base supplying the desired ion in a medium in which the salt precipitates or in aqueous medium and then lyophilizing.

As shown above, the amino or imino acid portion of the molecule of the products of formula I is in the L-configuration. An asymmetric center is also present in the acylalkylaminocarbonyl portion of the molecule when $R_3$ is other than hydrogen. Thus, the compounds of formula I can exist in diastereoisomeric forms or in mixtures thereof. The above described processes can utilize racemates, enantiomers or diastereomers as starting materials. When diastereomeric products are prepared, they can be separated by conventional chromatographic or fractional crystallization methods.

The products of formula I wherein the imino acid ring is monosubstituted give rise to cistrans isomerism. The configuration of the final product will depend upon the configuration of the $R_7$, $R_8$ and $R_9$ substituent in the starting material of formula XIV.

The compounds of formula I, and the pharmaceutically acceptable salts thereof, are hypotensive agents. They inhibit the conversion of the decapeptide angiotensin I to angiotensin II and, therefore, are useful in reducing or relieving angiotensin related hypertension. The action of the enzyme renin on angiotensinogen, a pseudoglobulin in blood, produces angiotensin I. Angiotensin I is converted by angiotensin converting enzyme (ACE) to angiotensin II. The latter is an active pressor substance which has been implicated as the causative agent in several forms of hypertension in various mammalian species, e.g., humans. The compounds of this invention intervene in the angiotensinogen→(renin)→angiotensin I→ angiotensin II sequence by inhibiting angiotensin converting enzyme and reducing or eliminating the formation of the pressor substance angiotensin II. Thus by the administration of a composition containing one (or a combination) of the compounds of this invention, angiotensin dependent hypertension in a species of mammal (e.g., humans) suffering therefrom is alleviated. A single dose, or preferably two to four divided daily doses, provided on a basis of about 0.1 to 100 mg. per kilogram of body weight per day is appropriate to reduce blood pressure. The substance is preferably administered orally, but parenteral routes such as the subcutaneous, intramuscular, intravenous or intraperitoneal routes can also be employed.

The compounds of this invention can also be formulated in combination with a diuretic for the treatment of hypertension. A combination product comprising a compound of this invention and a diuretic can be administered in an effective amount which comprises a total daily dosage of about 30 to 600 mg., preferably about 30 to 330 mg. of a compound of this invention, and about 15 to 300 mg., preferably about 15 to 200 mg. of the diuretic, to a mammalian species in need thereof. Exemplary of the diuretics contemplated for use in combination with a compound of this invention are the thiazide diuretics, e.g., chlorothiazide, hydrochlorothiazide, flumethiazide, hydroflumethiazide, bendroflumethiazide, methylclothiazide, trichloromethiazide, polythiazide or benzthiazide as well as ethacrynic acid, ticrynafen, chlorothalidone, furosemide, musolimine, bumetanide, triamterene, amiloride and spironolactone and salts of such compounds.

The compounds of formula I can be formulated for use in the reduction of blood pressure in compositions such as tablets, capsules or elixirs for oral administration, or in sterile solutions or suspensions for parenteral administration. About 10 to 500 mg. of a compound of formula I is compounded with physiologically acceptable vehicle, carrier, excipient, binder, preservative, stabilizer, flavor, etc., in a unit dosage form as called for by accepted pharmaceutical practice. The amount of active substance in these compositions or preparations in such that a suitable dosage in the range indicated as obtained.

The compounds of formula I wherein X is

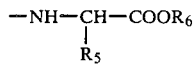

also possess enkephalinase inhibition activity and are useful as analgesic agents. Thus, by the administration of a composition containing one or a combination of such compounds of formula I or a pharmaceutically acceptable salt thereof, pain is alleviated in the mammalian host. A single dose, or preferably two to four divided daily doses, provided on a basis of about 0.1 to about 100 mg. per kilogram of body weight per day, preferably about 1 to about 50 mg. per kilogram per day, produces the desired analgesic activity. The composition is preferably administered orally but parenteral routes such as subcutaneous can also be employed.

The following examples are illustrative of the invention. Temperatures are given in degrees centigrade.

EXAMPLE 1

(±)-1-[[[3-(Benzoylamino)-2-oxo-4-phenylbutyl]-methylamino]carbonyl]-L-proline (a)

[3-(Benzoylamino)-2-oxo-4-phenylbutyl]-methylcarbamic acid, phenylmethyl ester

N-methyl-N-[(phenylmethoxy)carbonyl]-glycine (2.23 g., 10 mmole) is dissolved in 30 ml. of tetrahydrofuran and cooled in an ice-bath. Oxalyl chloride (1 ml., 11.5 mmole) is added followed by 2 drops of dimethylformamide. After stirring for 30 minutes in the ice-bath, the mixture is then stirred at room temperature for an hour. To this 0.25 ml. of oxalyl chloride is added. The mixture is evaporated, redissolved in 15 ml. of tetrahydrofuran, and stirred in an ice bath. A solution of 2-phenyl-4-(phenylmethyl)-5-(4H)-oxazolone (3.1 g., 12.4 mmole) dissolved in 15 ml. of tetrahydrofuran is added to the above solution stirring in the ice-bath. Triethylamine (1.4 ml., 10 mmole) is added and the solution is stirred at room temperature overnight. The precipitated triethylamine hydrochloride salt is filtered off. Tetrahydrofuran is removed from the residue and it is then redissolved in pyridine (5 ml.) and p-dimethylamino pyridine (20 mg.) is added. After stirring at room temperature for 3 hours, acetic acid (5 ml.) is added and the reaction mixture is kept at 105° for 30 minutes. The reaction mixture is then evaporated, the residue is dissolved in ethyl acetate, and washed with aqeuous sodium bicarbonate and water. After trituration with ethyl acetate/hexane, 2.2 g. of homogeneous [3-(benzoylamino)-2-oxo-4-phenylbutyl]methylcarbamic acid, phenylmethyl ester is obtained; m.p. 140°–141°.

(b)

(±)-N-[3-(Methylamino)-2-oxo-1-(phenylmethyl)-propyl]benzamide, hydrochloride

[3-(Benzoylamino)-2-oxo-4-phenylbutyl]methylcarbamic acid, phenylmethyl ester (0.5 g.) is dissolved in ethanol (50 ml.) containing 1N hydrochloric acid (2 ml.). Palladium carbon catalyst (10%, 100 mg.) is added and hydrogenation is continued overnight. The reaction mixture is then filtered, evaporated, dissolved in water, and lyophilized to 300 mg. of (±)-N-[3-(methylamino)-2-oxo-1-(phenylmethyl)propyl]benzamide, hydrochloride as a homogeneous white powder.

(c)

(±)-1-[[[3-(Benzoylamino)-2-oxo-4-phenylbutyl]methylamino]carbonyl]-L-proline, phenylmethyl ester L-Proline, phenylmethyl ester, hydrochloride (300 mg., 1.25 mmole) is dissolved in 5 ml. of methylene chloride and N-methyl morpholine (0.35 ml., 3.13 mmole) is added. To this solution stirring at −20°, 12% phosgene solution in benzene (2 ml. approximately 1.9 mmole) is added. Stirring is continued at −20° for 30 minutes. The mixture is then evaporated, the residue is suspended in methylene chloride (5 ml.) and (±)-N-[3-(methylamino)-2-oxo-1- (phenylmethyl)propyl]benzamide, hydrochloride (250 mg., 0.76 mmole) is added followed by N-methyl morpholine (0.22 ml., 2 mmole). The reaction mixture is stirred overnight. It is then evaporated, the residue is dissolved in ethyl acetate and washed with saturated sodium bicarbonate, dilute hydrochloric acid, and water. The ethyl acetate solution after evaporation is chromatographed over silica gel using the solvent system, ethyl acetate:benzene (4:6) to give (±)-1-[[[3-(benzoylamino)-2-oxo-4-phenylbutyl]-methylamino]carbonyl]-L-proline, phenylmethyl ester (37%) as an oil.

(d) (±)-1-[[[3-(Benzoylamino)-2-oxo-4-phenylbutyl]-methylamino]carbonyl]-L-proline The phenylmethyl ester product from part (c) (1.0 g., 1.9 mmole) is dissolved in absolute ethanol (75 ml.). Palladium carbon catalyst (10%, 100 mg.) is added and hydrogenation is continued for 48 hours. The mixture is then filtered, evaporated and chromatographed over silica gel using the solvent system chloroform: methanol:acetic acid (9.0:0.5:0.5) to give 400 mg. of (±)-1-[[[3-(benzoylamino)-2-oxo-4-phenylbutyl]methylamino]carbonyl]-L-proline; m.p. 75°–95°;

$R_f = 0.27$ [silica gel, chloroform:methanol:acetic acid (9.0:0.5:0.5)].

Anal. calc'd. for $C_{24}H_{27}N_3O_5 \cdot 0.54\ H_2O$: C, 64.52; H, 6.32; N, 9.41.

Found: C, 64.52; H, 6.29; N, 9.25.

EXAMPLES 2–59

Following the procedure of Example 1 the carboxyalkylamine shown in Col. I is converted to its acid chloride and then reacted with the oxazolone of Col. II. Removal of the benzyloxycarbonyl protecting group gives the intermediate shown in Col. III. Treatment with the acid chloride amino or imino acid ester of Col. IV gives the ester product shown in Col V. Removal of the $R_6$ ester group yields the final product wherein $R_6$ is hydrogen.

Col. I

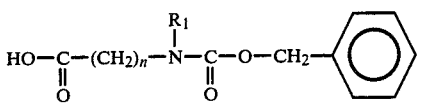

Col. II

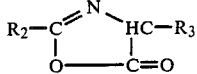

Col. III

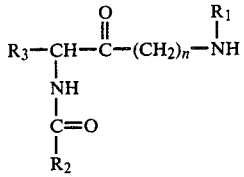

Col. IV

Col. V

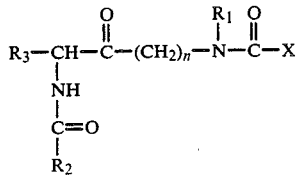

| Example | R₁ | n | R₂ | R₃ | X |
|---|---|---|---|---|---|
| 2 | H₃C— | 2 |  |  |  |
| 3 | H₅C₂— | 1 |  |  | 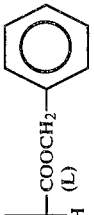 |
| 4 | H₃C— | 1 |  | H— |  |
| 5 | F₃C— | 2 |  |  |  |
| 6 | Cl₃CH₂C— | 1 |  |  |  |

-continued

| Example | R₁ | n | R₂ | R₃ | X |
|---|---|---|---|---|---|
| 7 | benzyl (PhCH₂–) | 2 | PhCH₂– | Ph(CH₂)₂– | –N(CH₂–)–CH(COOCH₂Ph)(H) (L), with CH₂–CH(N₃)– branch |
| 8 | H₃C– | 1 | Ph– | PhCH₂– | –N(CH₂–)–CH(COOCH₂Ph)(H) (L), with CH₂–CH(cyclohexyl)– branch |
| 9 | H₃C–(CH₂)₃– | 2 | Ph– | PhCH₂– | –N(CH₂–)–CH(COOCH₂Ph)(H) (L), with CH₂–CH(Ph)– branch |
| 10 | H₅C₂– | 1 | 2-thienyl | PhCH₂– | –N(CH₂–)–CH(COOCH₂Ph)(H) (L), with CH₂–C(F)(F)(CF...)– branch |
| 11 | H– | 1 | 2-furyl | Ph(CH₂)₂– | –N(CH₂–)–CH(COOCH₂Ph)(H) (L), with CH₂–C(CH₃)(OCH₃)(OCH₃)– branch |

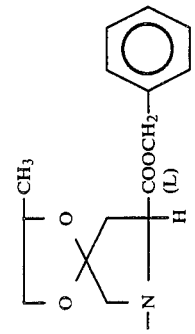

-continued
| Example | R₁ | n | R₂ | R₃ | X |
|---|---|---|---|---|---|
| 22 | H₃C— | 2 | phenyl | F₃C— |  |
| 23 | F₃C— | 1 | phenyl | phenyl-(CH₂)₃— |  |
| 24 | H₃C— | 1 | pyridyl | phenyl-CH₂— |  |
| 25 | H₅C₂— | 2 | phenyl-(CH₂)₃— | phenyl |  |
| 26 | H₃C— | 2 | phenyl | phenyl-(CH₂)₄— |  |
| 27 | H₃C— | 1 | phenyl | phenyl-(CH₂)₃— |  |

-continued

| Example | R₁ | R₂ | n | R₃ | X |
|---|---|---|---|---|---|
| 34 | PhCH₂OCOCHN(H₂C)₄-C(=O)- | Ph | 2 | PhCH₂- | dithiolane-CH(COOCH₂Ph)(H) (L) connected to -N- |
| 35 | 4-(H₂CO)C₆H₄-CH₂- | Ph | 1 | PhCH₂- | cyclohexyl-CH₂-CH(COOCH₂Ph)(H) (L) connected to -N- |
| 36 | 3,4-bis(H₂CO)-C₆H₃-CH₂- (with OPh) | thienyl | 1 | Ph-(CH₂)₂- | -N-CH(COOCH₂Ph)(H) (L) (propyl chain) |
| 37 | indol-3-yl-CH₂- | pyridyl | 2 | PhCH₂- | -N-CH(COOCH₂Ph)(H) (L) (propyl chain) |
| 38 | N-benzyl-imidazol-CH₂- | Ph | 1 | thienyl-CH₂- | tetrahydroisoquinoline-CH(COOCH₂Ph)(H) (L) |

-continued
| Example | R₁ | n | R₂ | R₃ | X |
|---|---|---|---|---|---|
| 39 | 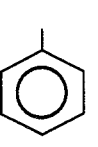 | 1 | 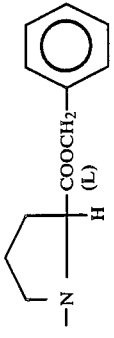 |  | 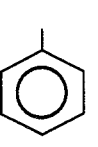 |
| 40 | H₃C— | 1 | 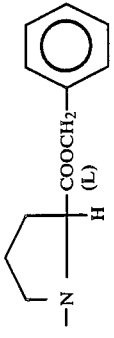 |  | 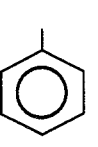 |
| 41 | H₃C— | 1 | 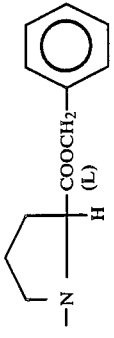 |  | 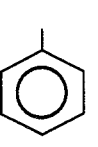 |
| 42 | H₃C— | 1 | 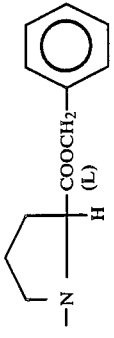 |  | 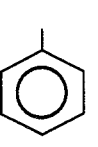 |
| 43 | H₃C— | 1 | 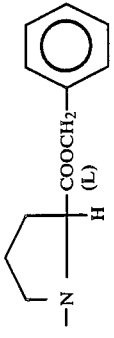 |  | 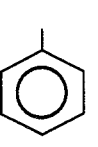 |
| 44 | F₃C— | 2 | 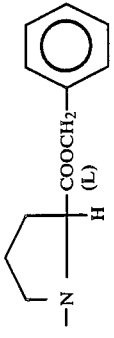 |  | —NH—CH—COOCH₂— (L) / CH₃ |

-continued

| Example | R₁ | n | R₂ | R₃ | X |
|---|---|---|---|---|---|
| 45 | C₆H₅-CH₂- | 1 | C₆H₅- | H- | -NH-CH(L)-COOCH₂-C₆H₅ with CH₂-CH(CH₃)₂ side chain |
| 46 | H₅C₂- | 1 | C₆H₅- | 2-furyl-CH₂- | -NH-CH(L)-COOCH₂-C₆H₅ with CH₂-C₆H₄-OCH₂-C₆H₅ side chain |
| 47 | H₃C- | 1 | C₆H₅- | C₆H₅-CH₂- | -NH-CH(L)-COOCH₂-C₆H₅ with CH₂-C₆H₃(OCH₂C₆H₅)₂ side chain |

-continued
| Example | R₁ | n | R₂ | R₃ | X |
|---|---|---|---|---|---|
| 48 | H₃C— | 1 |  |  |  |
| 49 |  | 2 |  |  |  |
| 50 | H₃C— | 1 |  | H₃C—(H₂C)₅— |  |
| 51 | H₃C— | 1 |  |  |  |

-continued
| Example | $R_1$ | n | $R_2$ | $R_3$ | X |
|---|---|---|---|---|---|
| 52 | $H_5C_2-$ | 1 | 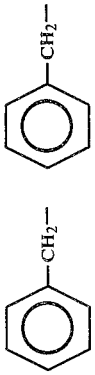 |  | 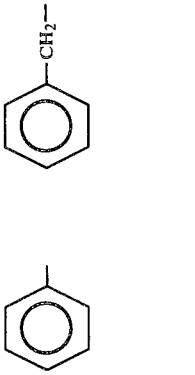 |
| 53 | $H_3C-$ | 2 |  | 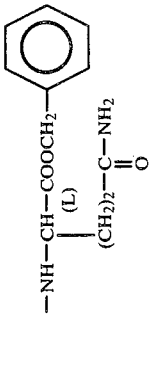 | 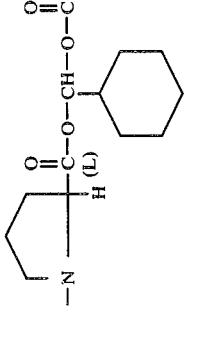 |
| 54 | $H_3C-$ | 1 |  |  |  |
| 55 | $H_3C-$ | 1 |  |  |  |
| 56 | $H_3C-$ | 2 | | | |

-continued

| Example | R₁ | n | R₂ | R₃ | X |
|---|---|---|---|---|---|
| 57 | F₃C— | 1 | phenyl | thiophen-2-yl-(CH₂)₂— | —N(lysine backbone with —C(=O)—O—CH₂—O—C(=O)—C(CH₃)₃) (L) |
| 58 | H₃C— | 1 | phenyl | 4-Cl-C₆H₄-CH₂— | —N(lysine backbone with —C(=O)—O—CH₂—O—C(=O)—C₆H₅) (L) |
| 59 | H₃C—(H₂C)₃— | 2 | phenyl | C₆H₅-CH₂— | —N(lysine backbone with —C(=O)—O— attached to 2-benzoylphenyl) (L) |

The $R_1$ protecting groups in Examples 17, 33 to 36, 38 and 39, the $R_3$ protecting groups in Examples 40 and 41, and the $R_5$ protecting groups in Examples 46, 47, and 49 to 52 are removed as the last step in the synthesis. The $R_6$ ester groups shown in Examples 54 to 59 are not removed.

EXAMPLE 60

(±)-1-[[[4-(Benzoylamino)-3-oxo-5-phenylpentyl]-methylamino]carbonyl]-L-proline (a) 3-(Methylamino)propanoic acid, methyl ester Methyl amine (66 ml.) in ethanol is chilled with stirring in an ice-bath. Methyl acrylate (45 ml.) is added dropwise over a period of 20 minutes. The bath is removed after one hour and after 4 hours the reaction mixture is concentrated in vacuo. The liquid is distilled at 15 mm. of Hg. at 61°–63° to give 18 g. of 3-(methylamino)propanoic acid, methyl ester.

(b) 1-[[(3-Methoxy-3-oxopropyl)methylamino]-carbonyl]-L-proline, 1,1-dimethylethyl ester L-Proline, 1,1-dimethylethyl ester (8.55 g.) is taken up into 200 ml. of methylene chloride with stirring at −20°. A solution of phosgene in benzene (12.5% by weight, 60 ml.) is added followed by 8.25 ml. of N-methyl morpholine. After 30 minutes at −20° the reaction mixture is concentrated in vacuo. The residue is taken up into 100 ml. of methylene chloride with stirring in an ice-bath. To this 7.0 g. of 3-(methylamino)-propanoic acid, methyl ester is added followed by N-methyl morpholine (5.5 ml.). After one hour the ice-bath is removed and the reaction mixture is kept at room temperature overnight. The reaction mixture is then concentrated in vacuo, taken up into ethyl acetate and washed with 10% potassium bisulfate and saturated sodium bicarbonate to yield 14.9 g. of crude product. Crystallization from ether/hexane yields 10.7 g. of 1-[[(3-methoxy-3-oxopropyl)methylamino]carbonyl]-L-proline, 1,1-dimethylethyl ester; m.p. 70°–71°.

(c) 1-[[(2-Carboxyethyl)methylamino]carbonyl]-L-proline, 1,1-dimethylethyl ester 1-[[(3-Methoxy-3-oxopropyl)methylamino]-carbonyl]-L-proline, 1,1-dimethylethyl ester (7.2 g.) is taken up into 47.7 ml. of methanol to which 28.6 ml. of 1N sodium hydroxide is added with stirring. After 2.5 hours the methanol is removed in vacuo. The aqueous phase is acidified with dilute hydrochloric acid and extracted into ethyl acetate to give 7.1 g. of crude product. Crystallization from ether/hexane yields 6.1 g. of 1-[[(2-carboxyethyl)-methylamino]carbonyl]-L-proline, 1,1-dimethylethyl ester; m.p. 69°–71°.

(d) (±)-1-[[[4-(Benzoylamino)-3-oxo-5-phenylpentyl]-methylamino]carbonyl]-L-proline, 1,1-dimethylethyl ester 1-[[[(2-Carboxyethyl)methylamino]carbonyl]-L-proline, 1,1-dimethylethyl ester (900 mg.) is taken up into 10.5 ml. of tetrahydrofuran with stirring in an ice-bath. To this oxalyl chloride (0.3 ml.) is added followed by 2 drops of dimethylformamide. After 20 minutes the ice-bath is removed. After one hour at room temperature the reaction mixture is concentrated to dryness in vacuo. The residue is taken up into 6 ml. of tetrahydrofuran and while stirring in an ice-bath 2-phenyl-4-(phenylmethyl)-5(4H)-oxazolone (754 mg.) in 4.8 ml. of tetrahydrofuran is added dropwise followed by triethylamine (0.42 ml.). The reaction mixture is kept at room temperature overnight, the triethylamine hydrochloride salt is filtered off and the filtrate is concentrated to dryness. The residue is taken up into 3.0 ml. of pyridine and stirred for 3 hours with 9 mg. of 4-dimethylamino pyridine. Acetic acid (3 ml.) is added and the mixture is heated at 100°–105° for 30 minutes, concentrated in vacuo, taken up into ethyl acetate and washed with saturated sodium bicarbonate and dilute hydrochloric acid to yield 1.1 g. of crude product. Purification on a silica gel column eluting with ethyl acetate: hexane (2:1) gives 330 mg. of (±)-1-[[[4-(benzoylamino)-3-oxo-5-phenylpentyl]methylamino]carbonyl]-L-proline, 1,1-dimethylethyl ester.

(e) (±)-1-[[[4-(Benzoylamino)-3-oxo-5-phenylpentyl]-methylamino]carbonyl]-L-proline The t-butyl ester product from part (d) (300 mg.) is treated for 1.5 hours with 3 ml. of trifluoroacetic acid, concentrated in vacuo and triturated to a solid with ether/hexane to give 250 mg. of (±)-1-[[[4-benzoylamino)-3-oxo-5-phenylpentyl]methylamino]carbonyl]-L-proline; m.p. 38°–68°; $[\alpha]_D^{23} = -9.16°$ (c = 1.2, methanol); $R_f$ = 0.71 [silica gel, chloroform:methanol:acetic acid (9:0.5:0.5)].

Anal. calc'd. for $C_{25}H_{29}N_3O_5 \cdot 1.37H_2O$: C, 63.04; H, 6.72; N, 8.82

Found: C, 63.04; H, 6.29; N, 8.61.

EXAMPLES 61–82

Following the procedure of Example 60 but employing the substituted amine shown in Col. I and the acid chloride imino or amino acid ester shown in Col. II one obtains the intermediate shown in Col. III. Treatment with methanol and sodium hydroxide followed by treatment with oxalyl chloride and reaction with the oxazolone of Col. IV yields the ester product of Col. V. Removal of the $R_6$ ester group yields the products wherein $R_6$ is hydrogen.

Col. I

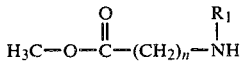

Col. II

Col. III

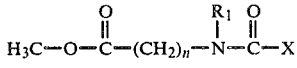

Col. IV

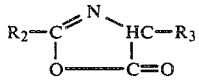

Col. V

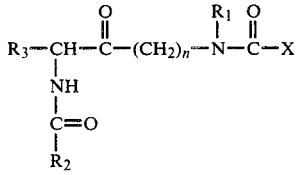

| Example | $R_3$ | $R_2$ | $R_1$ | X | n |
|---|---|---|---|---|---|
| 61 | 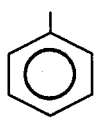 | 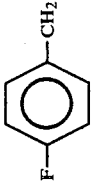 | $H_3C-$ | 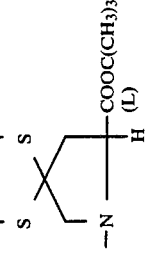 | 2 |
| 62 | 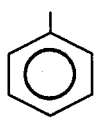 | 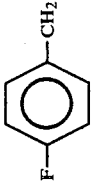 | $H_5C_2-$ | 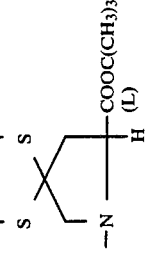 | 2 |
| 63 | 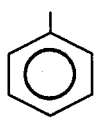 | 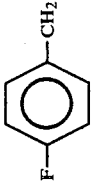 |  | 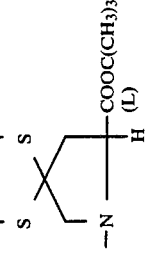 | 1 |
| 64 |  | 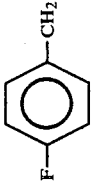 | $H_3C-$ | 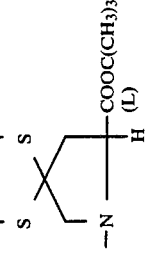 | 2 |
| 65 | 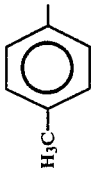 | 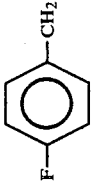 | $F_3C-$ | 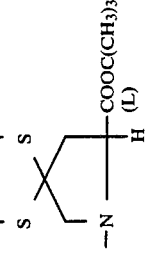 | 1 |

-continued

| Example | R$_3$ | R$_2$ | R$_1$ | X | n |
|---|---|---|---|---|---|
| 66 | H— | thiophen-2-yl-CH$_2$— | N-benzyl-imidazol-4-yl-CH$_2$— | —N(CH$_2$CH$_2$S–S)CH(COOC(CH$_3$)$_3$)H (L) | 2 |
| 67 | H$_3$C—(H$_2$C)$_3$— | pyridin-2-yl-CH$_2$— | H$_3$C— | —N(CH$_2$)$_4$CH(COOC(CH$_3$)$_3$)H (L) | 1 |
| 68 | pyridin-2-yl-(CH$_2$)$_2$— | phenyl— | C$_6$H$_5$-CH(NHCOOCH$_2$)C(O)— | —N(CH$_2$)$_4$CH(COOC(CH$_3$)$_3$)H (L) | 2 |
| 69 | phenyl— | benzyl-CH$_2$— | O$_2$N–HN–C(=NH)–NH–(CH$_2$)$_3$— | —N(CH$_2$C(S–S)CH$_2$)CH(COOC(CH$_3$)$_3$)H (L) | 2 |
| 70 | O$_2$N–HN–C(=NH)–NH–(CH$_2$)$_3$— | benzyl-CH$_2$— | H$_3$C— | —N(CH$_2$CH(SC$_6$H$_5$)CH$_2$)CH(COOC(CH$_3$)$_3$)H (L) | 1 |

-continued

| Example | R₃ | R₂ | R₁ | X | n |
|---|---|---|---|---|---|
| 71 | indol-3-ylmethyl (-CH₂-indole) | pyridin-4-ylmethyl (-CH₂-pyridine-4) | H₃C— | -N(CH(CH₂CH₂-O-Ph)-)CH(COOC(CH₃)₃)H (L) | 2 |
| 72 | 3,4-dimethoxybenzyl (-CH₂-C₆H₃(OCH₃)₂) with phenoxy | benzyl (-CH₂-Ph) | H₃C—(CH₂)₂— | -N(CH(CH₂CH₂-)-)CH(COOC(CH₃)₃)H (L) | 1 |
| 73 | benzyl (-CH₂-Ph) | benzyl (-CH₂-Ph) | cyclohexyl | —NH—CH(CH₂OCH₂Ph)—COOC(CH₃)₃ (L) | 1 |
| 74 | benzyl (-CH₂-Ph) | pyridin-2-ylmethyl (-CH₂-pyridine-2) | H₂C—Ph (benzyl) | —NH—CH(CH₂Ph)—COOC(CH₃)₃ (L) | 2 |
| 75 | thiophen-2-ylmethyl (-CH₂-thiophene) | benzyl (-CH₂-Ph) | H₃C— | —NH—CH(CH₂-C₆H₄-OCH₂Ph)—COOC(CH₃)₃ (L) | 2 |

-continued

| Example | R₃ | R₂ | R₁ | X | n |
|---|---|---|---|---|---|
| 76 | furan-2-yl-CH₂— | phenyl | H₃C— | —NH—CH(CH₂-N(CH=CH-phenyl))—COOC(CH₃)₃ (L) | 2 |
| 77 | cyclohexyl-CH₂— | phenyl | H₃C— | —NH—CH((CH₂)₄—NHCOCH₂-phenyl)—COOC(CH₃)₃ (L) | 1 |
| 78 | phenyl-(CH₂)₄— | phenyl | F₃C— | —NH—CH((CH₂)₂—C(O)NH₂)—COOC(CH₃)₃ (L) | 2 |
| 79 | phenyl-CH₂— | phenyl | H₃C— | dithiolane-proline-O-CH(cyclohexyl)-C(O)-O-C₂H₅ (L) | 1 |
| 80 | phenyl-CH₂— | phenyl | H₃C— | proline-C(O)-O-CH(CH(CH₃)₂)-C(O)-O-C₂H₅ (L) | 1 |
| 81 | pyridin-2-yl-(CH₂)₄— | phenyl | H₃C— | proline-C(O)-O-CH₂-O-C(CH₃)₃ (L) | 2 |

-continued

| Example | R$_3$ | R$_2$ | R$_1$ | X | n |
|---|---|---|---|---|---|
| 82 | ![thiophene-CH$_2$-] | ![phenyl] | H$_3$C— | —N(H)—CH(—C(=O)—O—CH(CH$_3$)—O—C(=O)—O—C$_2$H$_5$)— | 2 |

The $R_1$ protecting groups in Examples 66, 68 and 69, the $R_3$ protecting groups in Examples 70 and 72, and the $R_5$ protecting groups in Examples 73 and 75 to 77 are removed as the last step in the synthesis. The $R_6$ ester groups shown in Examples 79 to 82 are not removed.

EXAMPLE 83

(±)-1-[[[3-(Benzoylamino)-2-oxo-4-phenylbutyl]-methylamino]carbonyl]-L-proline, ethyl ester (±)-1-[[[3-(Benzoylamino)-2-oxo-4-phenylbutyl]methylamino]carbonyl]-L-proline (1 g.) is treated for 7 hours at room temperature with 10 ml. of 2N ethanol:-hydrochloric acid, concentrated in vacuo, taken up into ethyl acetate and washed neutral with 10% potassium bisulfate and saturated sodium bicarbonate to yield 900 mg. of crude product. This material is purified on silica gel column eluting with chloroform:methanol:acetic acid (90:3:3) to give 671 mg. of (±)-1-[[[3-(benzoylamino)-2-oxo-4-phenylbutyl]methylamino]carbonyl]-L-proline, ethyl ester; m.p. 40°–60°; $R_f$[chloroform:methanol:acetic acid (90:3:3)]=0.62.

Anal. calc'd. for $C_{26}H_{31}N_3O_5$ C, 66.24; H, 6.77; N, 8.91.

Found: C, 66.24; H, 6.75; N, 8.79.

EXAMPLE 84

(±)-1-[[[3-(Benzoylamino)-2-oxo-4-phenylbutyl]-methylamino]carbonyl]-L-proline, sodium salt (±)-1-[[[3-(Benzoylamino)-2-oxo-4-phenylbutyl]methylamino]carbonyl]-L-proline (1 mmole) is dissolved in water (50 ml.). Aqueous sodium bicarbonate (0.1N, 20 ml.) is added and the aqueous solution is lyophilized. It is then dissolved in water (10 ml.) and applied on a column (5 cm×60 cm.) of Sephadex chromatography gel G-10 and eluted with water. Fractions containing the desired product are pooled and lyophilized to obtain (±)-1-[[[3-(benzoylamino)-2-oxo-4-phenylbutyl]methylamino]carbonyl]-L-proline, sodium salt.

EXAMPLE 85

1000 tablets each containing the following ingredients

| | |
|---|---|
| (±)-1-[[[3-(Benzoylamino)-2-oxo-4-phenylbutyl]methylamino]carbonyl]-L-proline, sodium salt | 100 mg. |
| Corn starch | 50 mg. |
| Gelatin | 7.5 mg. |
| Avicel(microcrystalline cellulose) | 25 mg. |
| Magnesium stearate | 2.5 mg. | are prepared from sufficient bulk quantities by mixing the (±)-1-[[[3-(benzoylamino)-2-oxo-4-phenylbutyl]methylamino]carbonyl]-L-proline, sodium salt and corn starch with an aqueous solution of the gelatin. The mixture is dried and ground to a fine powder. The Avicel and then the magnesium stearate are admixed with granulation. This mixture is then compressed in a tablet press to form 1000 tablets each containing 100 mg. of active ingredient.

In a similar manner, tablets containing 100 mg. of the product of any of Examples 1 to 83 can be prepared.

A similar procedure can be employed to form tablets containing 50 mg. of active ingredient.

EXAMPLE 86

Two piece #1 gelatin capsules each containing 50 mg. of (±)-1-[[[4-(benzoylamino)-3-oxo-5-phenylpentyl]methylamino]carbonyl]-L-proline, sodium salt are filled with a mixture of the following ingredients:

| | |
|---|---|
| (±)-1-[[[4-(Benzoylamino)-3-oxo-5-phenylpentyl]methylamino]carbonyl]-L-proline, sodium salt | 50 mg. |
| Magnesium stearate | 7 mg. |
| Lactose | 193 mg. |
| | 250 mg. |

In a similar manner capsules containing 50 mg. of the product of any of Examples 1 to 84 can be prepared.

EXAMPLE 87

An injectable solution is prepared as follows:

| | |
|---|---|
| (±)-1-[[[3-(Benzoylamino)-2-oxo-4-phenylbutyl]methylamino]carbonyl]-L-proline, sodium salt | 500 g. |
| Methyl paraben | 5 g. |
| Propyl paraben | 1 g. |
| Sodium chloride | 25 g. |
| Water for injection | 5 l |

The active substance, preservatives, and sodium chloride are dissolved in 3 liters of water for injection and then the volume is brought up to 5 liters. The solution is filtered through a sterile filter and aseptically filled into presterilized vials which are closed with presterilized rubber closures. Each vial contains 5 ml. of solution in a concentration of 100 mg. of active ingredient per ml. of solution for injecton.

In a similar manner, an injectable solution containing 100 mg. of active ingredient per ml. of solution can be prepared for the product of any Examples 1 to 83.

EXAMPLE 88

1000 tablets each containing the following ingredients:

| | |
|---|---|
| (±)-1-[[[3-(Benzoylamino)-2-oxo-4-phenylbutyl]methylamino]carbonyl]-L-proline, sodium salt | 100 mg. |
| Avicel | 100 mg. |
| Hydrochlorothiazide | 12.5 mg. |
| Lactose | 113 mg. |
| Cornstarch | 17.5 mg. |
| Stearic acid | 7 mg. |
| | 350 mg. | are prepared from sufficient bulk quantities by slugging the (±)-1-[[[3-(benzoylamino)-2-oxo-4-phenylbutyl]methylamino]carbonyl]-L-proline, sodium salt, Avicel, and a portion of the stearic acid. The slugs are ground and passed through a #2 screen, then mixed with the hydrochlorothiazide, lactose, cornstarch, and remainder of the stearic acid. The mixture is compressed into 350 mg. capsule shaped tablets in a tablet press. The tablets are scored for dividing in half.

In a similar manner, tablets can be prepared containing 100 mg. of the product of any of Examples 1 to 83.

What is claimed is:

1. A compound of the formula

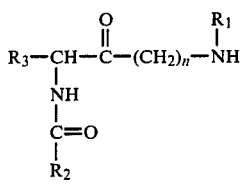

including its hydrochloride salt wherein
n is one or two;
$R_1$ is hydrogen, lower alkyl, halo substituted lower alkyl,

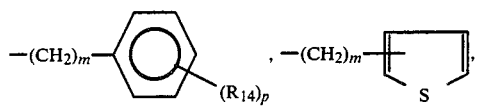

$—(CH_2)_m$—cycloalkyl, $—(CH_2)_2—NH_2$, $—(CH_2)_3—NH_2$, $—(CH_2)_4—NH_2$, $—(CH_2)_r—OH$, 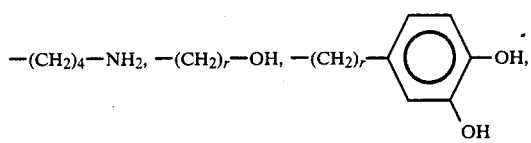

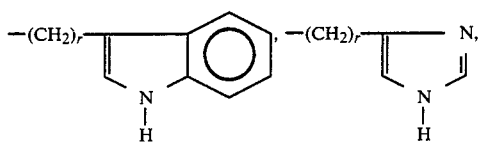

$—(CH_2)_r—SH$, $—(CH_2)_r—S$—lower alkyl,

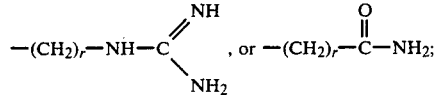

$R_2$ is 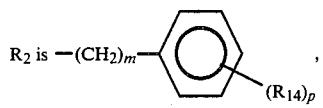

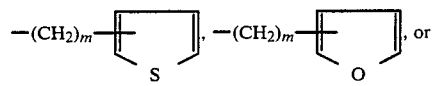, or

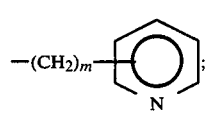;

$R_3$ is hydrogen, lower alkyl,

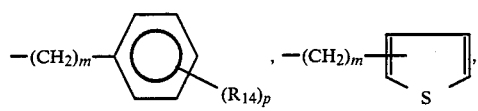

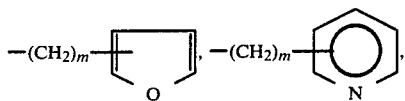

halo substituted lower alkyl, $—(CH_2)_m$-cycloalkyl,

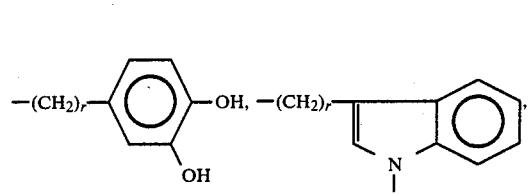

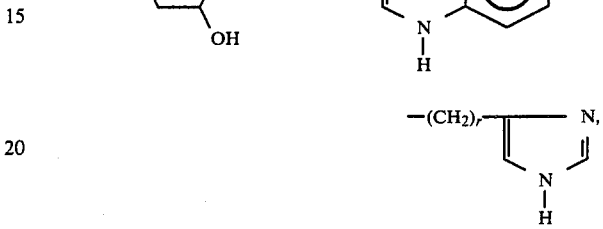

$—(CH_2)_r—NH_2$, $—(CH_2)_r—SH$, $—(CH_2)_r—OH$,
$—(CH_2)_r—S$-lower alkyl,

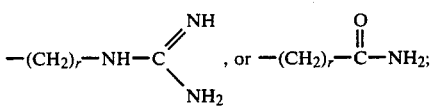

r is an integer from 1 to 4;
$R_{14}$ is hydrogen, lower alkyl of 1 to 4 carbons, lower alkoxy of 1 to 4 carbons, lower alkylthio of 1 to 4 carbons, chloro, bromo, fluoro, trifluoromethyl, or hydroxy;
m is zero, one, two, three, or four; and
p is one, two or three provided that p is more than one only if $R_{14}$ is hydrogen, methyl, methoxy, chloro, or fluoro.

2. A compound of claim 1 wherein
$R_2$ is

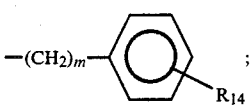

$R_3$ is

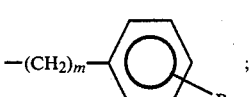

$R_1$ is hydrogen, straight or branched chain lower alkyl of 1 to 4 carbons, $—CF_3$, $—(CH_2)_2-NH_2$, $—(CH_2)_3-NH_2$, $—(CH_2)_4-NH_2$,

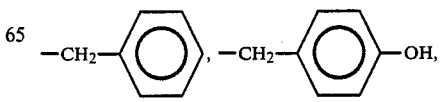

-continued
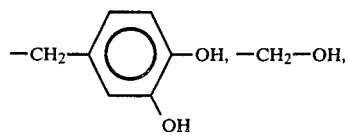
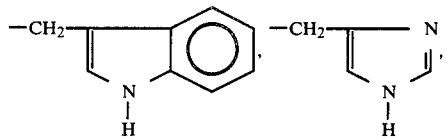
-continued
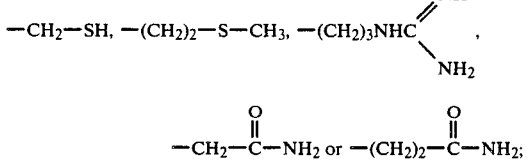
m is zero, one or two; and
R$_{14}$ is hydrogen, methyl, methoxy, methylthio, chloro, bromo, fluoro, or hydroxy.
3. The hydrochloride salt of the compound of claim 2 wherein n is one; R$_2$ is phenyl; R$_3$ is benzyl; and R$_1$ is methyl.
* * * * *